United States Patent
Missana et al.

(10) Patent No.: US 6,916,339 B1
(45) Date of Patent: Jul. 12, 2005

(54) BREAST PROSTHESIS

(76) Inventors: Marie-Christine Missana, 9 bis rue Kléber F-94210, La Varenne Saint-Hilaire (FR); Arnaud Rochebiliere, 13 Boulevard de Strasbourg, F-83000 Toulon (FR)

(*) Notice: Subject to any disclaimer, the term of this patent is extended or adjusted under 35 U.S.C. 154(b) by 5 days.

(21) Appl. No.: 09/980,120

(22) PCT Filed: May 29, 2000

(86) PCT No.: PCT/FR00/01457

§ 371 (c)(1),
(2), (4) Date: Nov. 30, 2001

(87) PCT Pub. No.: WO00/74599

PCT Pub. Date: Dec. 14, 2000

(30) Foreign Application Priority Data

Jun. 2, 1999 (FR) .................................. 99 06929

(51) Int. Cl.[7] .............................................. A61F 2/12
(52) U.S. Cl. .............................................. 623/8; 623/7
(58) Field of Search ........................... 623/7, 8, 11.11, 623/23.64

(56) References Cited

U.S. PATENT DOCUMENTS

| 2,651,783 A | 9/1953 | Wright et al. |
| 3,665,520 A | 5/1972 | Perras et al. |
| 5,066,302 A | 11/1991 | Rice |

FOREIGN PATENT DOCUMENTS

| EP | 0115384 | 8/1984 |
| FR | 2677539 | 12/1992 |
| FR | 2726173 | 5/1996 |
| FR | 2735354 | 12/1996 |
| GB | 2040688 | 9/1980 |
| GB | 2136692 | 9/1984 |
| WO | 96/40003 | 12/1996 |

OTHER PUBLICATIONS

International Preliminary Examination Report for PCT/FR00/01457, with English language translation.

*Primary Examiner*—David J. Isabella
(74) *Attorney, Agent, or Firm*—Greenblum & Bernstein, P.L.C.

(57) ABSTRACT

The invention concerns an implantable breast prosthesis comprising a soft pouch capable of a containing filler substance such as a physiological serum or a silicone gel and which is made side-specific, so as to satisfy aesthetic requirements and for better matching the convexity of the thorax.

54 Claims, 6 Drawing Sheets

FIG_1

FIG_2 PRIOR ART

FIG_3

FIG_4

FIG_5

BREAST PROSTHESIS

CROSS-REFERENCE TO RELATED APPLICATIONS

The present application is a National Stage Application of International Application No. PCT/FR00/01457, filed May 29, 2000. Further, the present application claims priority under 35 U.S.C. § 119 of French Patent Application No. 99/06929 filed on Jun. 2, 1999.

BACKGROUND OF THE INVENTION

1. Field of the Invention

The invention relates to an implantable breast prosthesis adapted more particularly to breast augmentation surgery and breast reconstructive surgery.

2. Discussion of Background Information

Breast prostheses are generally constituted of a silicone-type elastomeric soft pouch which is filled with a more or less viscous fluid. In Europe, this fluid most often is a physiological serum-base fluid which is inserted into the pouch during implantation of the prosthesis through an appropriate opening in the pouch which is sealed after the filling. In the United States, in particular, silicone gels are also used, inserted into the pouch which is then sealed before implantation. A particular type of prosthesis is called an expander: these prostheses are implanted beneath the area of the tissues to be expanded, then are progressively filled by an appropriate valve system with a fluid such as a physiological serum. Several examples of embodiment of these conventional or expansion prostheses are found in the Patent Applications FR-2 735 354, FR-2 726 173, and FR-2 677 539.

Numerous prostheses are currently commercially available, these prostheses having so-called "high profile," "low profile", or "anatomical" round shapes. All of them attempt as close an approximation to the natural shape of the breast as possible, but none has fully succeeded. The round-shaped prostheses do not feel natural, are overly projecting in the upper and inner parts (in a known fashion, the volume of the breast, as well as that of the prosthesis can be resolved into four parts depending upon their position in relation to the bust). With respect to the so-called anatomical shape, they have a more adapted shape, but they can easily be positioned incorrectly within the surgical pocket, because their posterior surfaces (i.e., the area of the prosthesis to be placed in contact with the thorax, which is also called the placement) have an inadequate contact with the thorax.

SUMMARY OF THE INVENTION

The present invention is an improvement to the design of breast prostheses, this improvement aiming particularly at a more aesthetic aspect, which is closer to that of the natural breast, regardless of whether the person wearing the prosthesis is seating, standing, or laying down, and/or a greater ease in positioning the prosthesis correctly during implantation, and/or a more constant retention of the prosthesis once it is implanted in the correct position, and/or a greater comfort in wearing the prosthesis.

According to the invention there is provided a breast prosthesis comprising a soft pouch capable of containing a sufficiently fluid filling material, such as a silicone or hydrocolloid gel or a physiological serum, the prosthesis being made side-specific.

In the context of the invention, "made side-specific" means that, once filled, the pouch demarcates a volume that cannot be placed indifferently to the left or to the right on the person's thorax: therefore, one obtains a right prosthesis and a left prosthesis, which are as specific as the natural breasts, especially with respect to the geometry of the posterior surface of the pouch and/or that of the anterior surface thereof ("anterior", as opposed to "posterior," designates the surface created by the pouch turned to the side opposite the thorax).

In addition to this side-specific arrangement translating into differences in the geometry between the (lower and upper) outer parts, on the one hand, and the (lower and upper) inner parts on the other hand, one can advantageously provide an additional side-specific arrangement translating into differences in the geometry between the (inner and outer) lower parts, on the one hand, and the (inner and outer) upper parts on the other hand: thus, one can also distinguish, in each prosthesis of the invention, the "upper" portion and the "lower" portion, in the implantation position, which cannot be inverted.

In the context of the invention, a "pouch capable of containing" means either the complete prosthesis, with the pouch fully filled with the filling fluid, or the partially filled pouch, or yet the pouch still empty since, as mentioned hereinabove, the protheses, depending particularly on the type of filling fluid selected or the function of the prosthesis, are in the form of empty or pre-filled pouches before implantation. Preferably, it is a final prosthesis. Since the geometry of the pouch determines that of the prosthesis as a whole, once the pouch is filled, the invention is more clearly defined with reference to a filled pouch defining the volume approximating that of the breast.

Indeed, the inventors became aware that such a "side-specific arrangement", such an asymmetry was the solution to the problem of overcoming the disadvantages of the prostheses currently used.

This side-specific arrangement can be obtained at various levels, which can be alternative, or preferably cumulative and which can be seen by referring to the drawings.

Thus, a first level is the choice of an asymmetry of the pouch in the implantation position (for ease of understanding, the implantation position is that of a person standing or sitting with her bust straight), once filled, in relation to a plane P1 passing by the nipple E (the front pole of the anterior surface simulating the breast nipple) and by the lower D and upper B front edges. Thus, this characteristic takes into account the asymmetry of the breasts in relation to a vertical sagittal plane. Indeed, a natural breast is hemispherical only on a teenager. Subsequently, it spreads on the thorax wall and then progressively displays a more rounded and more protruding aspect in the lower and outer parts. The asymmetry according to the invention advantageously enables the volume of the lower outer part of the implanted prosthesis to be larger than that of the lower inner part and/or that of the upper outer part to be larger than that of the upper inner part.

Preferably, this asymmetry is defined by a difference in the dimensions between the projection of the distance EC between the nipple and the front inner edge, on the one hand, and the projection of the distance EA between the nipple and the front outer edge, on the other hand, the projections being made along a plane P2 perpendicular to the plane P1 passing by the aforementioned nipple and containing the nipple E as well as the front upper edge B. The ratio between these two projections is advantageously less than or equal to 0.95, especially in the range of between 0.8 and 0.9, or between 0.85 and 0.90. The preferred embodiment utilizes a ratio on the order of 0.875, which is most capable of reproducing the more outwardly projecting aspect of the natural breast, whereas the currently available prostheses have a ratio strictly equal to 1.

Conversely, it is preferable that the projection of the distance EC between the nipple E and the inner edge C be equal to or very close to the projection of the distance EA' between the nipple E and the rear outer edge A', along this same plane P2: this configuration especially allows obtaining an outer "overlap" of the filled pouch in the implantation position in relation to the posterior surface thereof, this overlap extending in particular between the lower D and upper B rear edges, which simulates the aspect of the natural breast at best.

Advantageously, the prosthesis is designed such that, along the plane P2 described hereinabove, the dimension of the projection of the distance BE between the upper edge B and the nipple E is greater than the dimension of the projection of the distance ED between the nipple and the lower edge D. The ratio r (BE/ED) is preferably at least 1.1, especially between 1.1. and 2, or between 1.3 and 1.5.

Incidentally, to obtain the aforementioned "outward" overlapping effect, it is advantageous to have the plane P5 tangent, at k (the rear outer edge) to the anterior surface of the prosthesis form, at k, with the plane P6 tangent, at said point k, to the posterior surface, an obtuse angle $\phi$, especially greater than 95 or 100°, in particular comprised between 91° and 120°, for example on the order of 115°.

Preferably, the prosthesis does not contain any axillary extension or the like.

A second level of side-specific arrangement relates to taking into account the natural convexity of the thorax in a horizontal plane (still with the understanding that the prosthesis is filled and in the implantation position). The current prostheses have a planar posterior surface. The incorrect positions, prosthetic rotations and aesthetic drawbacks observed after implantation are explained in particular by this choice: since the prostheses assume the shape of the thoracic plane only on an insufficient surface, they can easily move. Conversely, according to the invention, at least one concave curvature is preferably imparted to the posterior surface, in order to increase this contact surface, and therefore to improve the fit of the prosthesis on the thorax.

Advantageously, a first concave curvature is provided in a horizontal plane P3, this plane passing by the inner edge C, for example. In this case, the perpendicular projection GG' of the pole G of the posterior surface on the horizontal plane P4 containing the outer rear edge A' and the inner edge C, is at least 3 mm, especially at least 5 mm or 1 cm, for example 0.8–1.5 cm.

Still advantageously, the posterior surface can also have a concave curvature, in a vertical plane P9, this time, this vertical plane passing by the upper edge B, for example. In this case, the perpendicular projection HH' of the pole H of the posterior surface along this curvature on a vertical plane P10, perpendicular to P9 and passing by the upper edge B, is at least 2 mm, especially comprised between 3 and 6 mm.

It is with this double curvature that the posterior surface closely fits the curvature of the thorax at best. Advantageously, the first curvature is uninterrupted between the inner edge C and the outer rear edge A', and similarly, the second curvature is uninterrupted from the upper edge B to the rear lower edge D (i.e., with no inverted planar or curvature zone between the two points considered for each of the curvatures).

To obtain this non-planar posterior surface, it can be made more rigid, less deformable than the anterior surface, for example by selectively increasing the thickness of the wall of this surface.

A third level of side-specific arrangement relates to the "connection" zones between the prosthesis and the thorax: the completely symmetrical prostheses currently available generally do not take into account either that the natural breasts, especially in the inner zone and in the upper zone, connect to the thorax along a "gentle" slope and not in a quasi-perpendicular manner with respect to the thorax.

Conversely, according to the invention, one first provides to simulate this gentle slope connection in the upper zone of the prosthesis, by designing the prosthesis such that the planes P10 and P11 tangent to the posterior surface and to the anterior surface, respectively, of the pouch, once it is filled and in the implantation position at the upper edge B, form therebetween an angle less than or equal to 70°, especially less than or equal to 65 or 60°, for example on the order of 40°.

Alternatively or cumulatively, the invention also provides a gentle slope connection of the prosthesis with the thorax in the inner zone of the prosthesis: the pouch is designed such that the planes P7 and P8 tangent to the anterior surface and to the posterior surface, respectively, of the pouch, once it is filled and in the implantation position at the inner edge C, form therebetween an angle less than or equal to 70°, especially less than or equal to 65 or 60°, for example on the order of 40°.

The invention concerns the protheses having at least one level of side-specific arrangement and pertaining to the family of prostheses described in the present application. It relates to prostheses having all of the volumes commonly used in breast surgery, namely, prostheses which, once filled, have a volume ranging from 80 $cm^3$ to 700 $cm^3$.

The invention also provides for an implantable breast prosthesis which is specific to either a right breast side or a left breast side of a patient, the prosthesis comprising a soft pouch adapted to contain a filling material. The soft pouch comprises a posterior surface, an anterior surface, an inner zone and an outer zone. The posterior surface and the anterior surface form an angle $\beta$ in the inner zone of less than 70 degrees when the soft pouch is implanted and filled with the filling material. The soft pouch is specific to either the right breast side or the left breast side of the patient.

The filling material may comprise one of a silicone gel and a physiological serum. The soft pouch may be asymmetrical in relation to a plane which passes through an upper zone of the soft pouch, a nipple area of the soft pouch and a lower zone of the soft pouch, when the soft pouch is implanted in the patient and filled. The asymmetry may be defined by a difference in dimensions between a first distance and a second distance defined by a plane passing through the inner zone, the nipple area and the outer zone, whereby the plane passing through the inner zone, the nipple area and the outer zone is perpendicular to a plane passing through the upper zone, the nipple area and the lower zone. The first distance may be different from the second distance. The first distance may be defined between an edge of the inner zone and a point in the nipple area and the second distance may be defined between an edge of the outer zone and the point in the nipple area. A ratio r of the first distance to the second distance may be less than or equal to 0.95. The ratio r may be in the range of between 0.8 and 0.9. The ratio r may be in the range of between 0.85 and 0.9. The ratio r may be about 0.875. The soft pouch may further comprise a rear outer zone adjacent the outer zone, and wherein the plane passes through the inner zone, the nipple area, the outer zone and the rear outer zone. The prosthesis may further comprise a third distance being defined between an edge of the rear outer zone and a point in the nipple area, whereby the first distance is defined between the point in the nipple area and an edge of the inner zone, the first distance and the third distance being at least one of equal to each other and very close to each other.

The asymmetry may be defined by a difference in dimensions between a fourth distance and a fifth distance defined by a plane passing through the upper zone, the nipple area and the lower zone, whereby the plane passing through the upper zone, the nipple area and the lower zone is perpendicular to a plane passing through the inner zone, the nipple area and the outer zone. The fourth distance may be different from the fifth distance. The fourth distance may be defined between an edge of the upper zone and a point in the nipple area and wherein the fifth distance is defined between an edge of the lower zone and the point in the nipple area. The fourth distance may be greater than the fifth distance. A ratio r of the fourth distance to the fifth distance may be at least 1.1. The ratio r may be in the range of between 1.1 and 2. The ratio r may be in the range of between 1.3 and 1.5.

The soft pouch further may comprise an outer overlap portion in an area of the outer zone, when the soft pouch is implanted in the patient and filled. The outer overlap portion may extend to each of the upper zone and the lower zone. The outer overlap portion may comprise an anterior surface which forms an obtuse angle φ relative to the posterior surface. The angle φ may be greater than 95 degrees. The angle φ may be greater than 100 degrees. The angle φ may be in the range of between 91 degrees and 120 degrees. The angle φ may be 115 degrees.

The posterior surface may be at least one of concave and curved. The posterior surface may be at least one of concave and curved between an edge of the inner zone and an edge of the outer zone. The posterior surface may be at least one of concave and curved at least in an area of the inner zone.

A distance between a plane extending through an edge of the inner zone and an edge of the outer zone and a parallel plane extending through a point on the posterior surface that is farthest away from the plane extending through the edge of the inner zone and the edge of the outer zone may be at least 5 mm.

A distance between a plane extending through an edge of the inner zone and an edge of the outer zone and a parallel plane extending through a point on the posterior surface that is farthest away from the plane extending through the edge of the inner zone and the edge of the outer zone may be at least 1 cm.

The posterior surface may be at least one of concave and curved between an edge of an upper zone and an edge of a lower zone. The surface may be at least one of concave and curved at least in an area of an upper zone.

A distance between a plane extending through an edge of an upper zone and an edge of a lower zone and a parallel plane extending through a point on the posterior surface that is farthest away from the plane extending through the edge of the upper zone and the edge of the lower zone may be at least 1 mm.

A distance between a plane extending through an edge of an upper zone and an edge of a lower zone and a parallel plane extending through a point on the posterior surface that is farthest away from the plane extending through the edge of the upper zone and the edge of the lower zone may be at least 2 mm.

A distance between a plane extending through an edge of an upper zone and an edge of a lower zone and a parallel plane extending through a point on the posterior surface that is farthest away from the plane extending through the edge of the upper zone and the edge of the lower zone may be in the range of between 3 mm and 6 mm.

The anterior surface may be at least one of curved and convex.

A distance between a plane extending through an edge of an upper zone and an edge of a lower zone and a parallel plane extending through a point on the anterior surface that is farthest away from the plane extending through the edge of the upper zone and the edge of the lower zone may be in the range of between 3 cm and 7 cm.

A distance between a plane extending through an edge of an upper zone and an edge of a lower zone and a parallel plane extending through a point on the anterior surface that is farthest away from the plane extending through the edge of the upper zone and the edge of the lower zone may be on the order of 5 cm.

At least a portion of the posterior surface may be one of less deformable and more rigid than another portion of the soft pouch. The portion of the posterior surface that is one of less deformable and more rigid than another portion of the soft pouch may have a thicker surface than the other portion of the soft pouch.

The posterior surface and the anterior surface may form an angle δ in an upper zone of less than 70 degrees when the soft pouch is implanted and filled with the filling material. The angle δ may be less than 65 degrees. The angle δ may be less than 60 degrees. The angle δ may be about 40 degrees. The angle β may be less than 65 degrees. The angle β may be less than 60 degrees. The angle β may be about 40 degrees.

The soft pouch may comprise an elastomer. The elastomer may comprise silicone. The soft pouch may be adapted to be filled with the filling material either before or after being implanted into the patient. The implantable breast prosthesis may comprise an expansion prosthesis.

The invention also provides for an implantable breast prosthesis which is specific to either a right breast side or a left breast side of a patient, the prosthesis comprising a soft pouch adapted to contain a filling material. The soft pouch comprises a concave posterior surface, a convex anterior surface, an inner zone, an outer zone, an upper zone and a lower zone. The posterior surface and the anterior surface form an angle β in the inner zone of less than 70 degrees when the soft pouch is implanted and filled with the filling material. The posterior surface and the anterior surface form an angle δ in the upper zone of less than 70 degrees when the soft pouch is implanted and filled with the filling material. The soft pouch is specific to either the right breast side or the left breast side of the patient.

The invention also provides for an implantable breast prosthesis which is specific to either a right breast side or a left breast side of a patient, the prosthesis comprising a soft pouch adapted to contain a filling material. The soft pouch comprises a concave posterior surface, a convex anterior surface, an inner zone, an outer zone, an upper zone and a lower zone. The posterior surface and the anterior surface form an angle β in the inner zone of less than 70 degrees when the soft pouch is implanted and filled with the filling material. The posterior surface and the anterior surface form an angle δ in the upper zone of less than 70 degrees when the soft pouch is implanted and filled with the filling material. A nipple pole zone is defined on each of the posterior surface and the anterior surface. An axis is defined by a line passing through a point on each of the nipple zones of the posterior surface and the anterior surface, whereby the axis is perpendicular to a plane which extends from an edge of the inner zone to an edge of the outer zone. An upper outer part of the soft pouch is defined by a first plane extending through the upper zone and the lower zone, a second plane extending through the inner zone and the outer zone, an upper outer portion of the posterior surface and an upper outer portion of the anterior surface, whereby each of the first and second planes are perpendicular to each other. An upper inner part of the soft pouch is defined by the first plane, the second plane, an upper inner portion of the posterior surface and an upper inner portion of the anterior surface. A lower outer part of the soft pouch is defined by the first plane, the second plane, a lower outer portion of the posterior surface and a lower outer portion of the anterior surface. A lower inner part of the soft pouch is defined by the first plane, the second plane, a lower inner portion of the posterior surface and a lower inner portion of the anterior surface. Each of the upper outer part, the upper inner part, the lower outer part and the lower inner part have different volumes. The soft pouch is specific to either the right breast side or the left breast side of the patient.

BRIEF DESCRIPTION OF THE DRAWINGS

The details and advantageous characteristics of the invention will now become apparent from the following non-limiting example, by way of FIGS. 1–6.

DETAILED DESCRIPTION OF THE INVENTION

Figure 1:
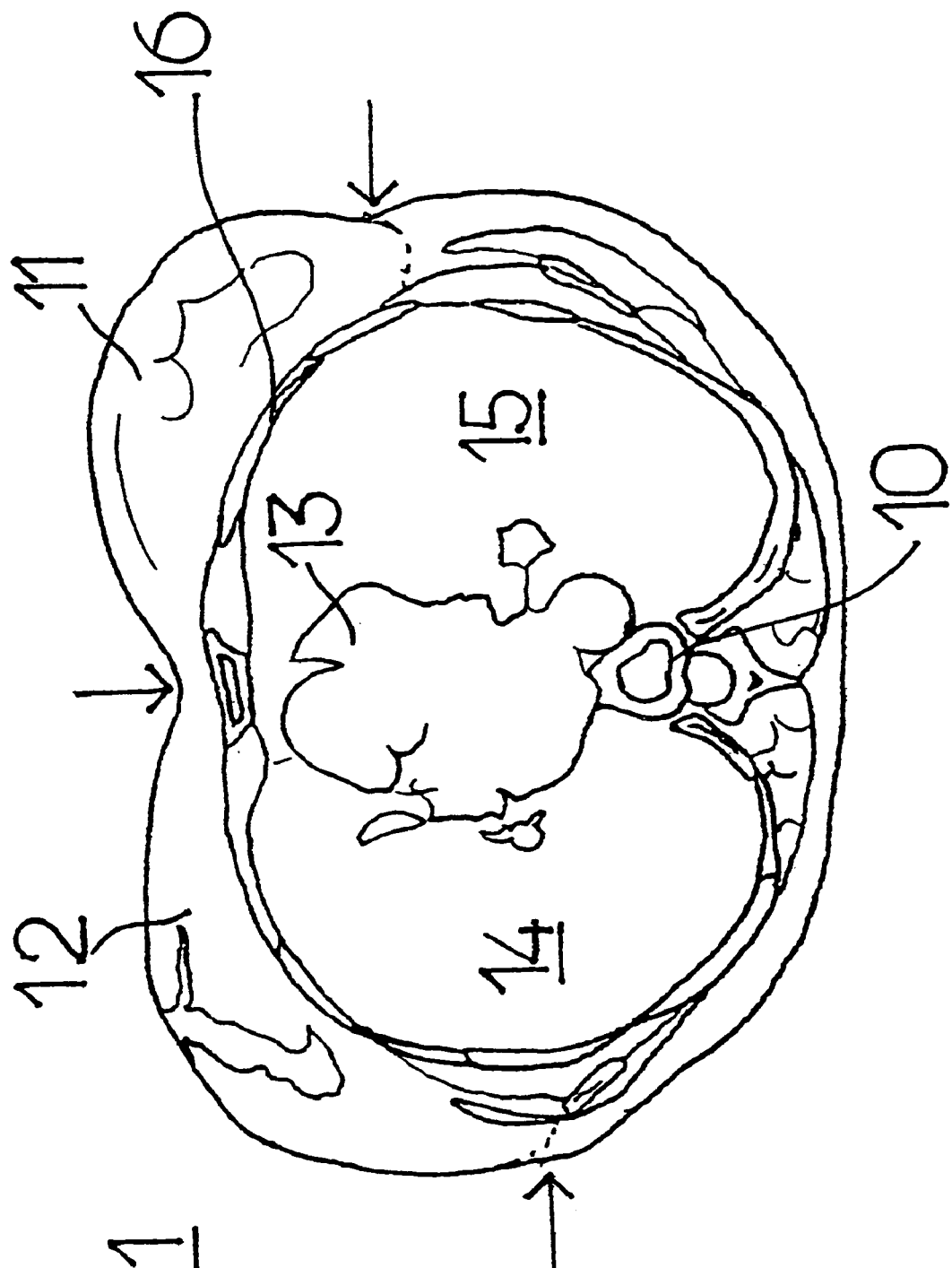
FIG. 1 schematically shows a transverse cross-section of a thorax with natural breasts.

FIG. 1 is a transverse cross-section of the thorax in a mediastinal window passing by the fourth dorsal vertebra, schematically shown from a scannographic illustration. One sees the spine 10, the two breasts 11 and 12, the mediastinum 13, the lung fields 14 and 15, the costal plane 16. It can be noted that the two breasts "spread" naturally on the thoracic plane 16 by assuming its convex shape. The arrows represent the inner and outer limits of the projection of the two areolar glands on the thorax.

Figure 2:
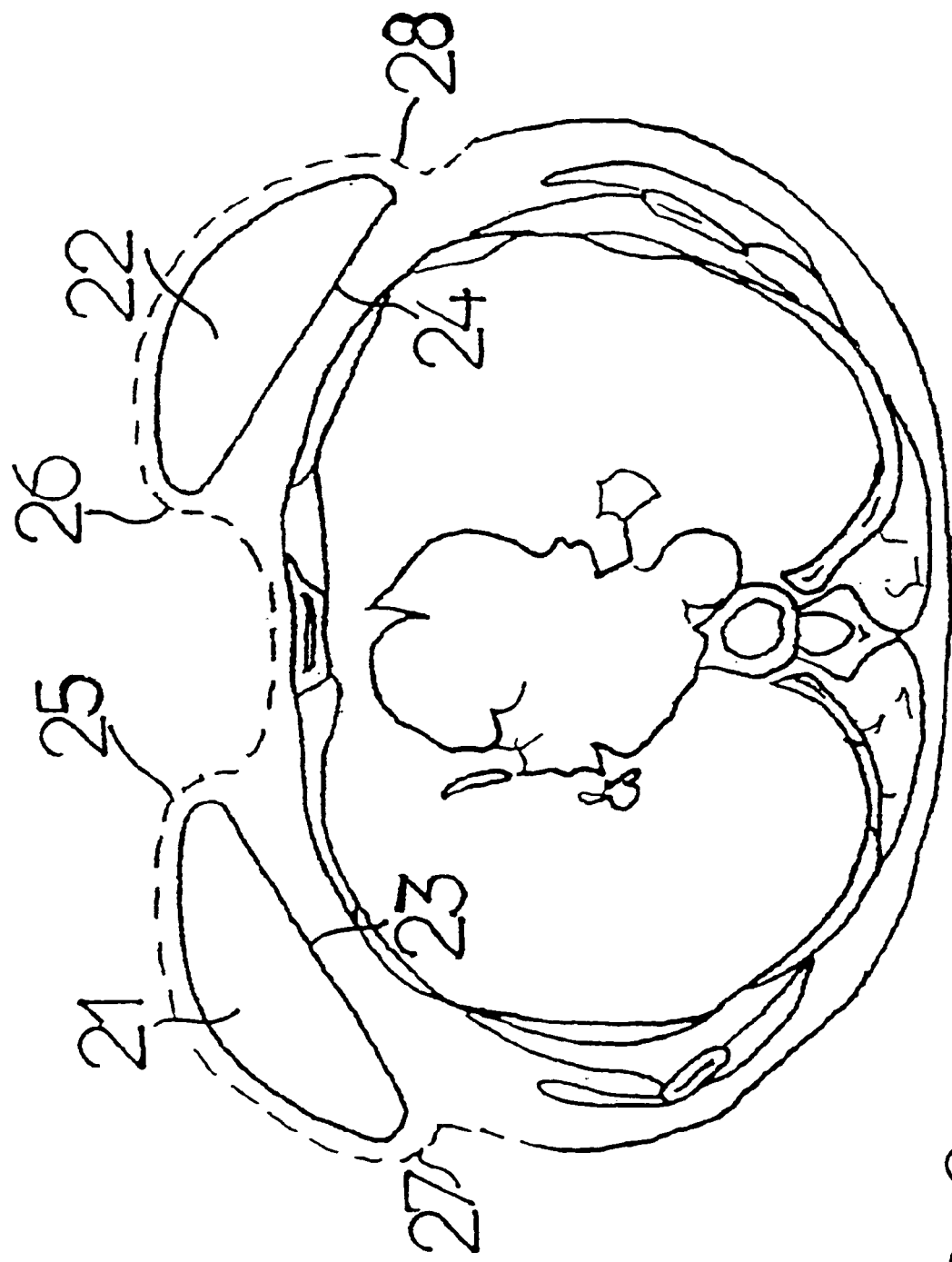
FIG. 2 shows the same cross-section with two prostheses according to the prior art.

FIG. 2 shows, along the same cross-section as in FIG. 1, some of the drawbacks of one type of (comparative) prosthesis that is currently commercially available: the prostheses 21 and 22 have planar posterior surfaces 23 and 24 which do not follow the curvature of the thorax. In addition, they create, in the inner zones 25 and 26 for connection with the thorax, an almost 90° angle with the thorax. In almost the same situation in the outer connection zones 27 and 28, the external appearance of the prosthesis is unaesthetic, on the one hand, and it is susceptible of moving in the pocket where it is implanted, increasing the unaesthetic effect and the discomfort for the person, on the other hand.

Figure 3:
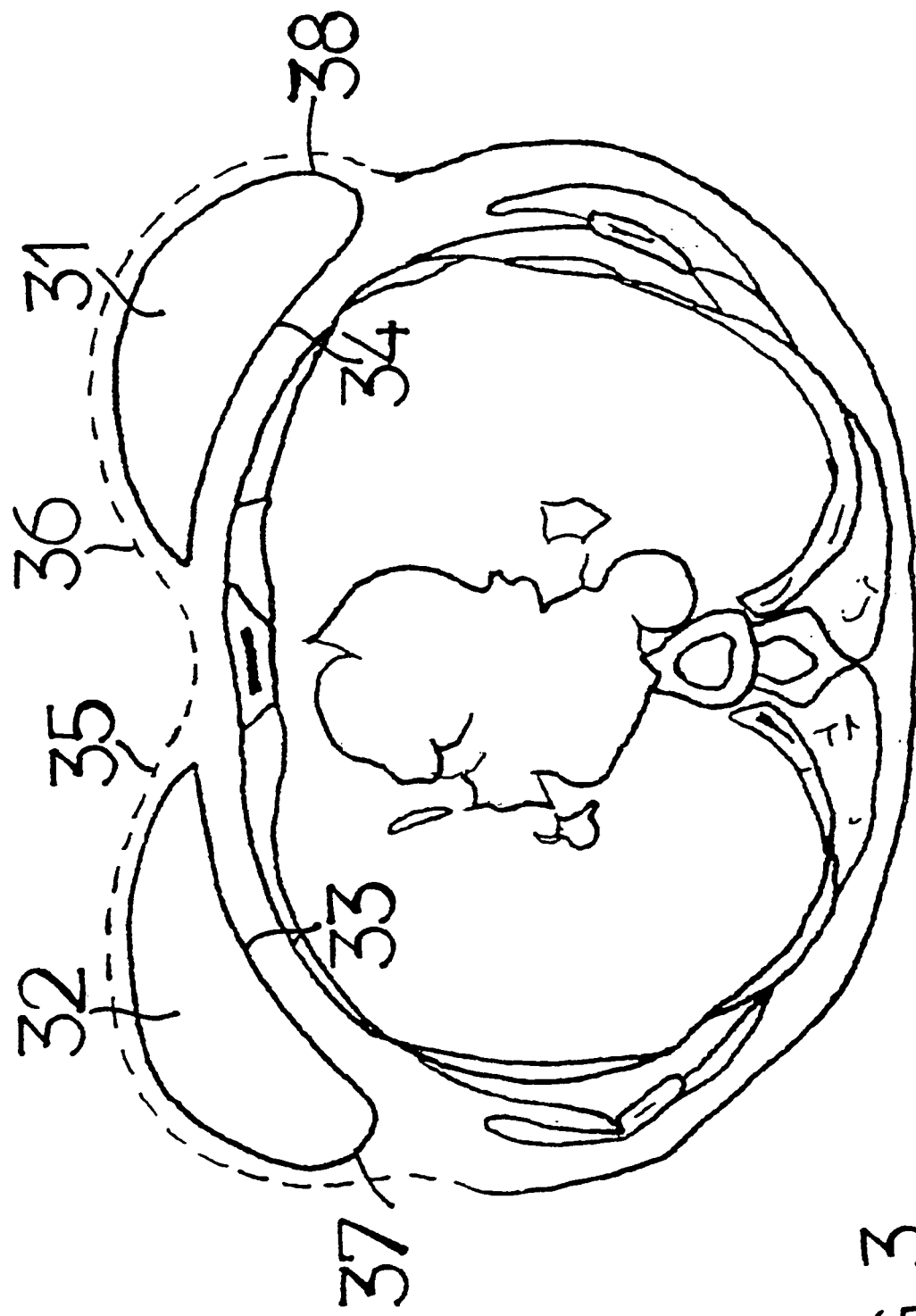
FIG. 3 shows the same cross-section with two prostheses according to the invention.

FIG. 3 shows the prostheses 31, 32 according to a preferred embodiment of the invention. They are much closer to the aspect of the breasts of FIG. 1, with a posterior surface 33, 34 assuming the convexity of the thorax as closely as possible, and connections in inner zones 35, 36 and in outer zones 37, 38 along a gentle slope. The prostheses 31, 32 have a volume that is better distributed and closer to the thoracic cage; as a result, they are much less susceptible of moving. It is also seen that the prostheses 31, 32, contrary to the prostheses 21, 22, of the prior art which are not interchangeable, are made side-specific, asymmetrical as are the natural breasts.

The following Figures will discuss the geometry of the prosthesis 31 in detail.

Figure 4:
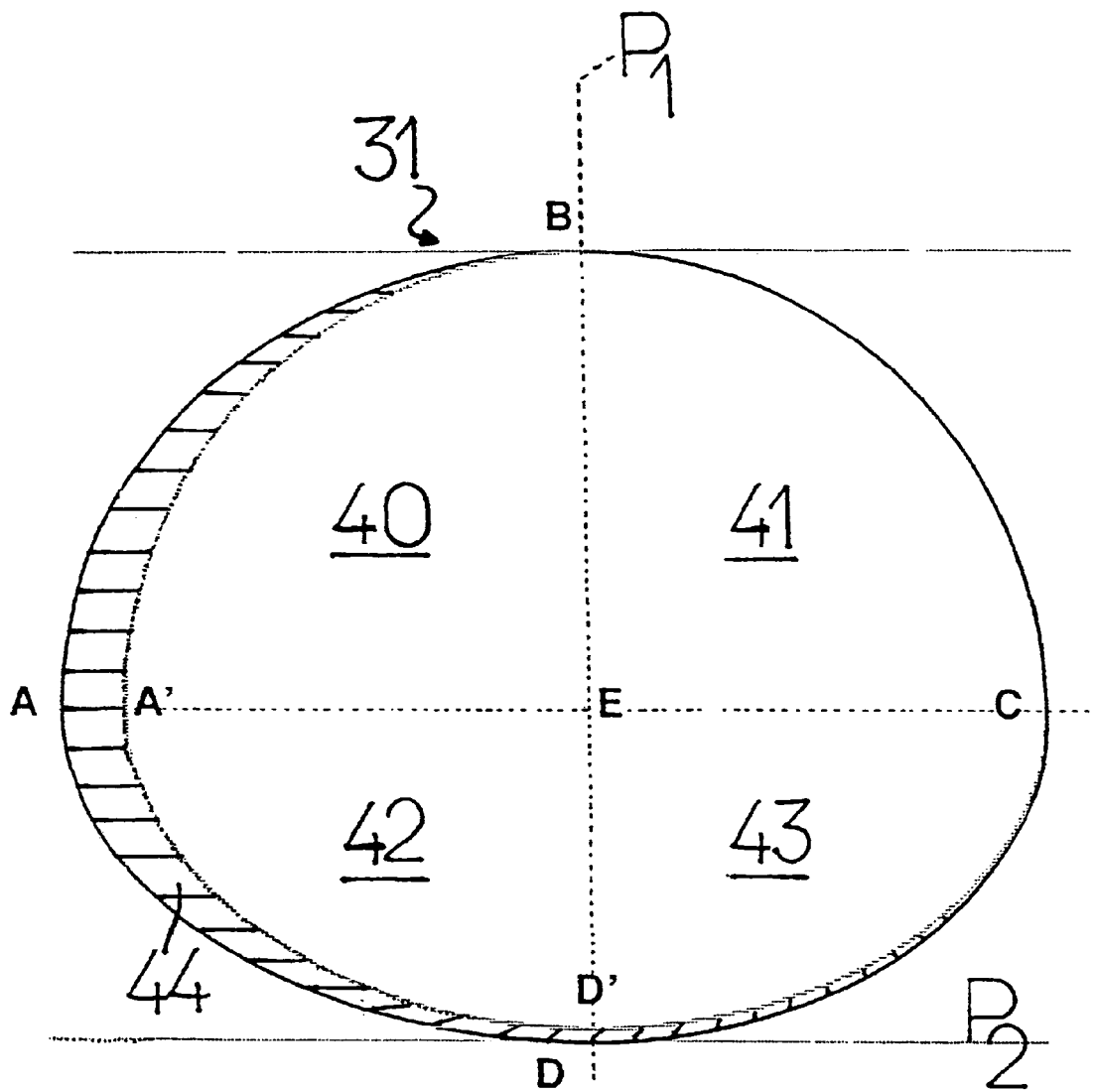
FIG. 4 shows a view of the anterior surface along a vertical plane of the right prosthesis according to the invention.

FIG. 4 therefore shows a front view of the right prosthesis 31 of FIG. 3. It is understood that from this representation, as well as all of the following ones, one can derive those of the left breast 32, which is the mirror construction in volume of the right prosthesis 31. This representation and the following ones are on a scale of 1:1.

The point E shown is the front pole of the prosthesis, which corresponds to the nipple of the natural breast, the point C is the inner edge (that which is going to be turned toward the other prosthesis in the implantation position), the points B and D are the upper and lower front edges, respectively, the point A is the front outer edge (as opposed to "inner"), the point A' is the rear outer edge and the point D' the rear lower edge. This is a prosthesis having a volume of about 480 cm$^3$.

The dimensions of the distances between these various points, measured in the plane P2, are as follows:

AA'=1 cm (length of the outer overlap)
A'C=14 cm (base of the prosthesis)
AC=15 cm (total width of the prosthesis)
BD=12 cm (total height of the prosthesis)
DD'=2 mm
A'E=EC=7 cm
AE=8 cm
BE=7 cm
ED=5 cm It is seen that the prosthesis does not have any symmetry in relation to the plane P1 passing by B, D, and E, and perpendicular to the plane P2 represented in the Figure: the distance EC is notably shorter than the distance AE, and the volumes of the upper 40 and lower 42 outer parts are larger than that of the volumes of the upper 41 and lower 43 inner parts. There is a hatched area 44 that corresponds to an overlap of the anterior surface in relation to the surface developed by the posterior surface, which translates into the distance separating the points A and A'. This overlap is most substantial in the vicinity of the points A and A', but it is seen that it extends up into the inner lower part 43 (the distance between D and D' is not negligible). The prosthesis also has an asymmetry between the volumes of the lower 42 and upper 40 outer parts, on the one hand, and between the volumes of the lower 43 and upper 41 inner parts, on the other hand, which translates into the difference between the distances BE and ED. In the present case, the ratio r (BE/ED) is 1.4. This ratio can be generally selected preferably between 1.1 and 2, especially between 1.3 and 1.5.

Figure 5:
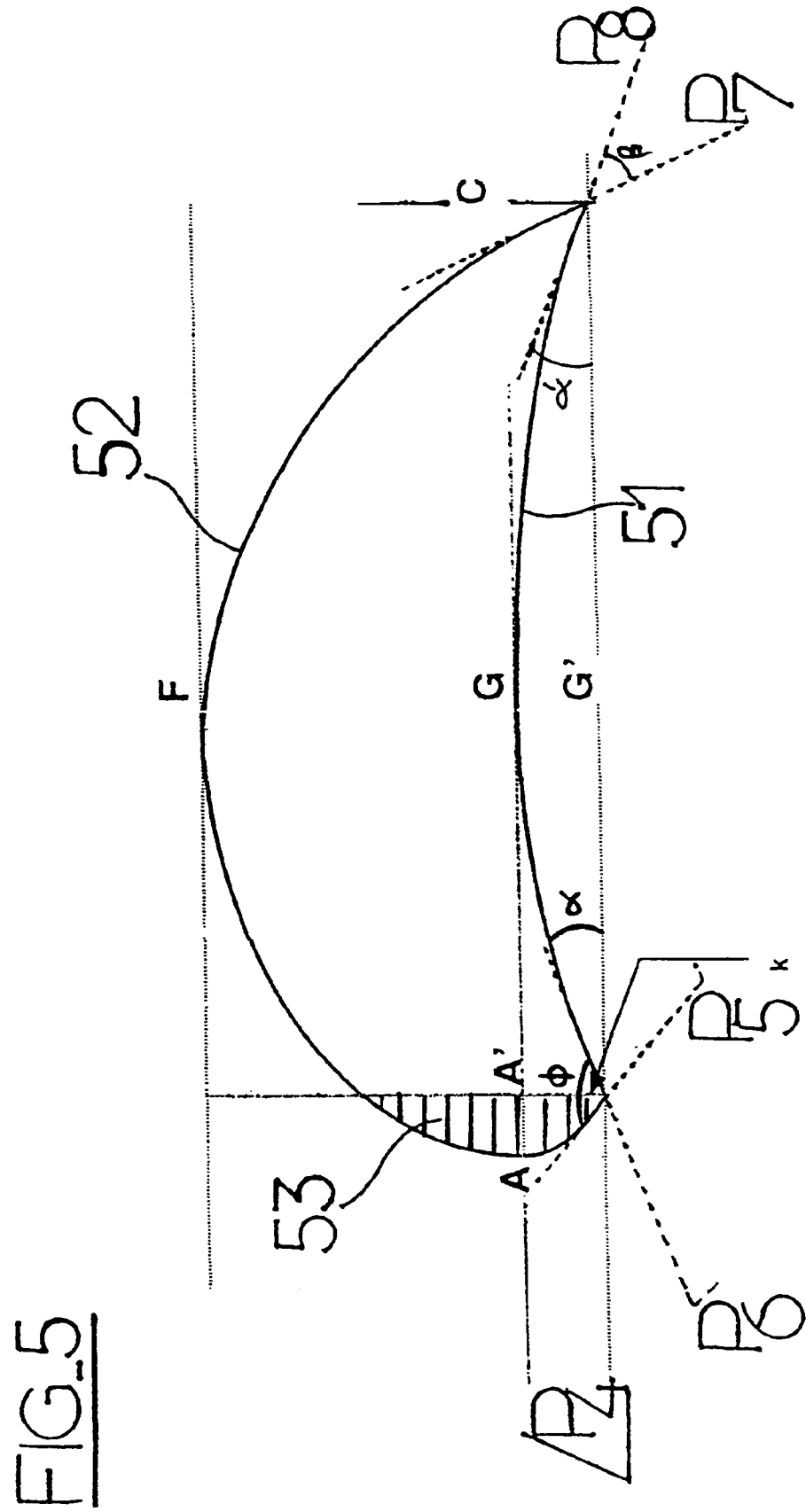
FIG. 5 shows a view of the prosthesis of FIG. 4 in a horizontal cross-section.

FIG. 5 is a horizontal cross-sectional view of the previous Figure. According to this cross-section, the point F is the pole of the anterior surface 52 and G the pole of the posterior surface 51. G' is the projection of G in the plane P4 which is the plane perpendicular to the plane of the cross-section, and which passes by k and C. It must be noted that the axes BD of FIG. 4 and FG of this Figure are perpendicular to one another, but with an off centering of about 1 cm. They do not intersect.

The distances between these various points are:
GG'=1.3 cm
FG=5 cm (front projection of the prosthesis)
kG'=6 cm
GC=8 cm Therefore, one can easily see that the posterior surface 51 has a uniform concavity extending between the points k and C. This concavity can be quantified by the distance GG' which is greater than 1 cm, and by the angles α and α' formed by the planes tangent to the posterior surface 51, at points k and C, with the plane P4. Here, the two angles α and α' on the outer and inner side are substantially identical (about 25°, which can be in the range of between 20° and 30°), but it could also be otherwise. It can be noted that G' is not in the middle of kC. There is an A'G/G'C ratio of about 0.75 (for example in the range of between 0.5 and 1). The hatched area 53 corresponds to the outer overlap designated by the reference numeral 44 in the previous Figure. This makes it possible to see more clearly that the prosthesis allows obtaining the natural effect of an outwardly projecting breast.

FIG. 5 also shows the gentle slope connection mentioned hereinabove, the connection between the inner edge C of the prosthesis and the thorax: thus, the plane P8 tangent to the posterior surface 51 at point C forms, together with the plane P7 tangent to the anterior surface at same point C, a small angle β, much less than 90°, here on the order of 40°.

FIG. 5 also shows that the outer overlap 53 also translates into an angle φ of about 115°, at point k, between the plane P5 passing by k and tangent to the anterior surface 52 and the plane P6 also passing by k and tangent to the posterior surface 51 of the prosthesis.

Figure 6:
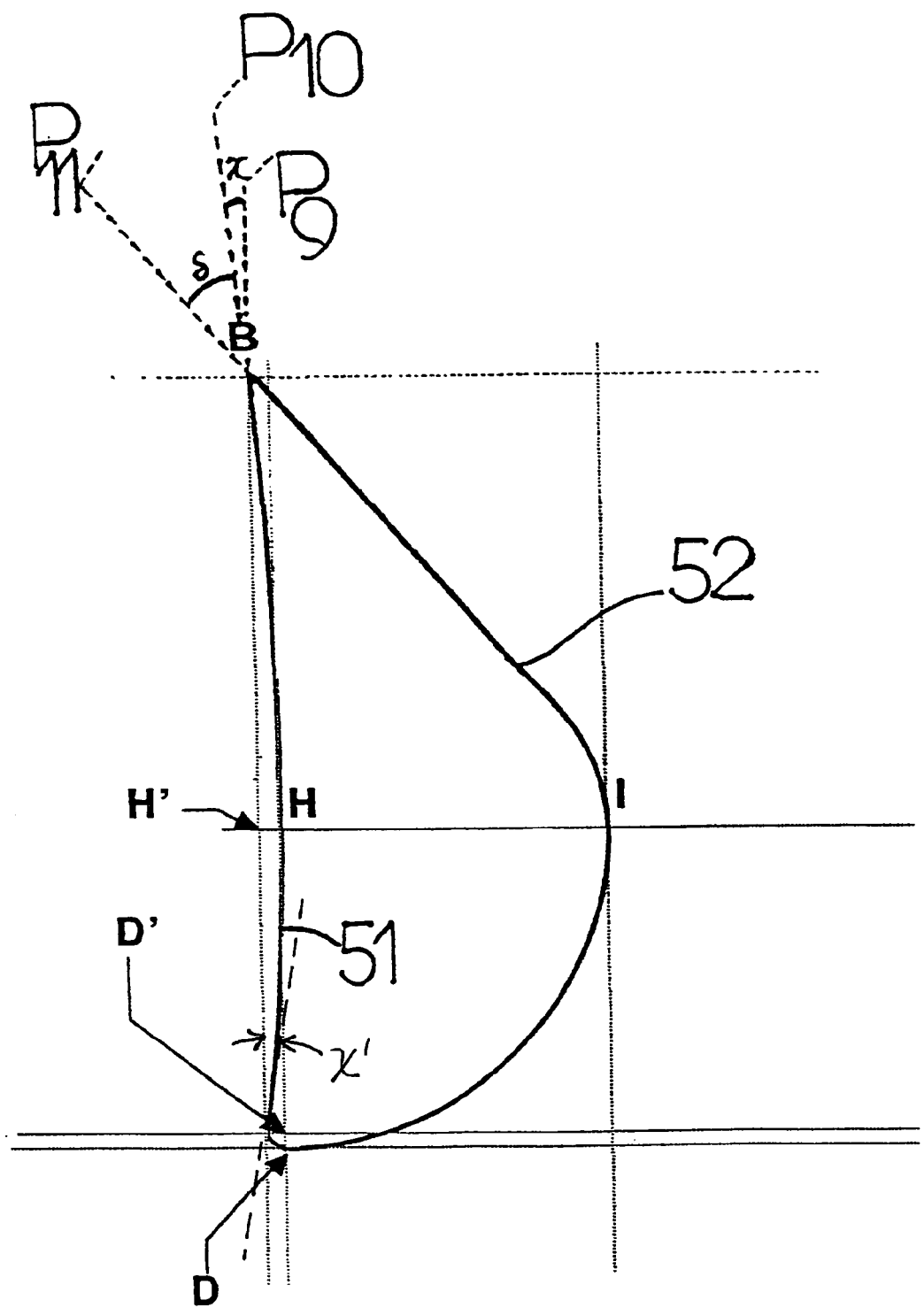
FIG. 6 shows a side view of the prosthesis of FIG. 4.

FIG. 6 is a side view of the prosthesis 31. The point I is the pole of the anterior 110 surface 52 along the plane of the Figure. The point H is the pole of the posterior surface 51 along the plane of the Figure. The point H' is the perpendicular projection of H on a vertical plane P9 passing by B and perpendicular to the plane of the Figure. The distances between these various points are as follows:
HH'=3.5 mm
HI=5 cm (front projection of the prosthesis)
HD=5 cm
H'B=7 cm
DD'=2 mm The posterior surface 51 has a second concavity in the plane of the Figure. This concavity can be quantified by the distance HH' which is greater than 1 mm, and by the angle χ formed by the plane P10 tangent to the posterior surface 51 at point B with the plane P9. (The situation is the same on the other side near point D' with regard to angle χ', the concavity extending from B up to D'). Here, the angles χ and χ' are each about 7°, and can be in the range of between 4° and 15°, for example.

FIG. 6 also makes it possible to see a second gentle slope connection on the upper zone of the prosthesis: at point B, the angle δ formed by the plane P10 explained hereinabove and the plane P11 tangent to the anterior surface 52 to point B is small, i.e., much less than 90° or 60°, and it is selected here to be about 38.5°.

The distance HI is an important characteristic of the prosthesis because it makes it possible to define the front projection of the prosthesis. In this specific example, it is 5 centimeters, but it can be selected more generally in a range of 3–7 centimeters.

In conclusion, this non-limiting example of prosthesis is the one that combines all of the characteristics of the invention for even closer an approximation to the aspect of the natural breast than before. Prostheses of various volumes can result from mere similarity. However, it remains consistent with the invention to provide prostheses that would not cumulate all of the methods for side-specific arrangement, (adaptation to the convexity of the thorax by a concave posterior surface and/or at least one "gentle slope connection", and/or an asymmetry in relation to a vertical plane passing by the nipple, and/or an outer "overlap" . . . ).

What is claimed is:

1. An implantable breast prosthesis which is specific to either a right breast side or a left breast side of a patient, the prosthesis comprising:
   a soft pouch adapted to contain a filling material;
   the soft pouch comprising a posterior surface, an anterior surface, an inner zone and an outer zone; and
   the posterior surface and the anterior surface forming an angle β in the inner zone of less than 70 degrees when the soft pouch is implanted and filled with the filling material,
   wherein the soft pouch is specific to either the right breast side or the left breast side of the patient.

2. The prosthesis claim 1, wherein the filling material comprises one of a silicone gel and a physiological serum.

3. The prosthesis of claim 1, wherein the soft pouch is asymmetrical in relation to a plane which passes through an upper zone of the soft pouch, a nipple area of the soft pouch and a lower zone of the soft pouch, when the soft pouch is implanted in the patient and filled.

4. The prosthesis of claim 3, wherein the asymmetry is defined by a difference in dimensions between a first distance and a second distance defined by a plane passing through the inner zone, the nipple area and the outer zone, whereby the plane passing through the inner zone, the nipple area and the outer zone is perpendicular to a plane passing through the upper zone, the nipple area and the lower zone.

5. The prosthesis of claim 4, wherein the first distance is different from the second distance.

6. The prosthesis of claim 4, wherein the first distance is defined between an edge of the inner zone and a point in the nipple area and wherein the second distance is defined between an edge of the outer zone and the point in the nipple area.

7. The prosthesis of claim 6, wherein a ratio r of the second distance to the first distance is less than or equal to 0.95.

8. The prosthesis of claim 7, wherein the ratio r is in the range of between 0.8 and 0.9.

9. The prosthesis of claim 8, wherein the ratio r is in the range of between 0.85 and 0.9.

10. The prosthesis of claim 9, wherein the ratio r is about 0.875.

11. The prosthesis of claim 4, wherein the soft pouch further comprises a rear outer zone adjacent the outer zone, and wherein the plane passes through the inner zone, the nipple area, the outer zone and the rear outer zone.

12. The prosthesis of claim 11, further comprising a third distance being defined between an edge of the rear outer zone and a point in the nipple area, whereby the first distance is defined between the point in the nipple area and an edge of the inner zone, the first distance and the third distance being at least one of equal to each other and very close to each other.

13. The prosthesis of claim 3, wherein the asymmetry is defined by a difference in dimensions between a fourth distance and a fifth distance defined by a plane passing through the upper zone, the nipple area and the lower zone, whereby the plane passing through the upper zone, the nipple area and the lower zone is perpendicular to a plane passing through the inner zone, the nipple area and the outer zone.

14. The prosthesis of claim 13, wherein the fourth distance is different from the fifth distance.

15. The prosthesis of claim 13, wherein the fourth distance is defined between an edge of the upper zone and a point in the nipple area and wherein the fifth distance is defined between an edge of the lower zone and the point in the nipple area.

16. The prosthesis of claim 15, wherein the fourth distance is greater than the fifth distance.

17. The prosthesis of claim 16, wherein a ratio r of the fourth distance to the fifth distance is at least 1.1.

18. The prosthesis of claim 17, wherein the ratio r is in the range of between 1.1 and 2.

19. The prosthesis of claim 18, wherein the ratio r is in the range of between 1.3 and 1.5.

20. The prosthesis of claim 1, wherein the soft pouch further comprises an outer overlap portion in an area of the outer zone, when the soft pouch is implanted in the patient and filled.

21. The prosthesis of claim 20, wherein the outer overlap portion extends to each of the upper zone and the lower zone.

22. The prosthesis of claim 20, wherein the outer overlap portion comprises an anterior surface which forms an obtuse angle $\phi$ relative to the posterior surface.

23. The prosthesis of claim 22, wherein the angle $\phi$ is greater than 95 degrees.

24. The prosthesis of claim 23, wherein the angle $\phi$ is greater than 100 degrees.

25. The prosthesis of claim 20, wherein the angle $\phi$ is in the range of between 91 degrees and 120 degrees.

26. The prosthesis of claim 25, wherein the angle $\phi$ is 115 degrees.

27. The prosthesis of claim 1, wherein the posterior surface is at least one of concave and curved.

28. The prosthesis of claim 27, wherein the posterior surface is at least one of concave and curved between an edge of the inner zone and an edge of the outer zone.

29. The prosthesis of claim 27, wherein the posterior surface is at least one of concave and curved at least in an area of the inner zone.

30. The prosthesis of claim 27, wherein a distance between a plane extending through an edge of the inner zone and an edge of the outer zone and a parallel plane extending through a point on the posterior surface that is farthest away from the plane extending through the edge of the inner zone and the edge of the outer zone is at least 5 mm.

31. The prosthesis of claim 25, wherein a distance between a plane extending through an edge of the inner zone and an edge of the outer zone and a parallel plane extending through a point on the posterior surface that is farthest away from the plane extending through the edge of the inner zone and the edge of the outer zone is at least 1 cm.

32. The prosthesis of claim 27, wherein the posterior surface is at least one of concave and curved between an edge of an upper zone and an edge of a lower zone.

33. The prosthesis of claim 27, wherein the posterior surface is at least one of concave and curved at least in an area of an upper zone.

34. The prosthesis of claim 27, wherein a distance between a plane extending through an edge of an upper zone and an edge of a lower zone and a parallel plane extending through a point on the posterior surface that is farthest away from the plane extending through the edge of the upper zone and the edge of the lower zone is at least 1 mm.

35. The prosthesis of claim 27, wherein a distance between a plane extending through an edge of an upper zone and an edge of a lower zone and a parallel plane extending through a point on the posterior surface that is farthest away from the plane extending through the edge of the upper zone and the edge of the lower zone is at least 2 mm.

36. The prosthesis of claim 27, wherein a distance between a plane extending through an edge of an upper zone and an edge of a lower zone and a parallel plane extending through a point on the posterior surface that is farthest away from the plane extending through the edge of the upper zone and the edge of the lower zone is in the range of between 3 mm and 6 mm.

37. The prosthesis of claim 1, wherein the anterior surface is at least one of curved and convex.

38. The prosthesis of claim 37, wherein a distance between a plane extending through an edge of an upper zone and an edge of a lower zone and a parallel plane extending through a point on the anterior surface that is farthest away from the plane extending through the edge of the upper zone and the edge of the lower zone is in the range of between 3 cm and 7 cm.

39. The prosthesis of claim 37, wherein a distance between a plane extending through an edge of an upper zone and an edge of a lower zone and a parallel plane extending through a point on the anterior surface that is farthest away from the plane extending through the edge of the upper zone and the edge of the lower zone is on the order of 5 cm.

40. The prosthesis of claim 1, wherein at least a portion of the posterior surface is one of less deformable and more rigid than another portion of the soft pouch.

41. The prosthesis of claim 40, wherein the portion of the posterior surface that is one of less deformable and more rigid than another portion of the soft pouch has a thicker surface than the other portion of the soft pouch.

42. The prosthesis of claim 1, wherein the posterior surface and the anterior surface form an angle $\delta$ in an upper zone of less than 70 degrees when the soft pouch is implanted and filled with the filling material.

43. The prosthesis of claim 42, wherein the angle $\delta$ is less than 65 degrees.

44. The prosthesis of claim 43, wherein the angle $\delta$ is less than 60 degrees.

45. The prosthesis of claim 44, wherein the angle $\delta$ is about 40 degrees.

46. The prosthesis of claim 1, wherein the angle $\beta$ is less than 65 degrees.

47. The prosthesis of claim 46, wherein the angle $\beta$ is less than 60 degrees.

48. The prosthesis of claim 47, wherein the angle $\beta$ is about 40 degrees.

49. The prosthesis of claim 1, wherein the soft pouch comprises an elastomer.

50. The prosthesis of claim 49, wherein the elastomer comprises silicone.

51. The prosthesis of claim 1, wherein the soft pouch is adapted to be filled with the filling material either before or after being implanted into the patient.

52. The prosthesis of claim 1, wherein the implantable breast prosthesis comprises an expansion prosthesis.

53. An implantable breast prosthesis which is specific to either a right breast side or a left breast side of a patient, the prosthesis comprising:

a soft pouch adapted to contain a filling material;

the soft pouch comprising a concave posterior surface, a convex anterior surface, an inner zone, an outer zone, an upper zone and a lower zone;

the posterior surface and the anterior surface forming an angle β in the inner zone of less than 70 degrees when the soft pouch is implanted and filled with the filling material; and the posterior surface and the anterior surface forming an angle δ in the upper zone of less than 70 degrees when the soft pouch is implanted and filled with the filling material, wherein the soft pouch is specific to either the right breast side or the left breast side of the patient.

54. An implantable breast prosthesis which is specific to either a right breast side or a left breast side of a patient, the prosthesis comprising:

a soft pouch adapted to contain a filling material;

the soft pouch comprising a concave posterior surface, a convex anterior surface, an inner zone, an outer zone, an upper zone and a lower zone;

the posterior surface and the anterior surface forming an angle β in the inner zone of less than 70 degrees when the soft pouch is implanted and filled with the filling material;

the posterior surface and the anterior surface forming an angle δ in the upper zone of less than 70 degrees when the soft pouch is implanted and filled with the filling material;

a nipple pole zone being defined on each of the posterior surface and the anterior surface;

an axis being defined by a line passing through a point on each of the nipple zones of the posterior surface and the anterior surface, whereby the axis is perpendicular to a plane which extends from an edge of the inner zone to an edge of the outer zone;

an upper outer part of the soft pouch being defined by a first plane extending through the upper zone and the lower zone, a second plane extending through the inner zone and the outer zone, an upper outer portion of the posterior surface and an upper outer portion of the anterior surface, whereby each of the first and second planes are perpendicular to each other;

an upper inner part of the soft pouch being defined by the first plane, the second plane, an upper inner portion of the posterior surface and an upper inner portion of the anterior surface;

a lower outer part of the soft pouch being defined by the first plane, the second plane, a lower outer portion of the posterior surface and a lower outer portion of the anterior surface; and a lower inner part of the soft pouch being defined by the first plane, the second plane, a lower inner portion of the posterior surface and a lower inner portion of the anterior surface, wherein each of the upper outer part, the upper inner part, the lower outer part and the lower inner part have different volumes, and wherein the soft pouch is specific to either the right breast side or the left breast side of the patient.

* * * * *